United States Patent [19]
Pong et al.

[11] Patent Number: 5,391,167
[45] Date of Patent: Feb. 21, 1995

[54] ARTICULATING EXTERNAL FIXATION DEVICE

[75] Inventors: Henry Pong; Thomas J. McCauley, both of West Palm Beach, Fla.

[73] Assignee: Ortho-Motion, Inc., Coral Springs, Fla.

[21] Appl. No.: 938,621

[22] Filed: Sep. 1, 1992

[51] Int. Cl.$^6$ .............................................. A61B 17/60
[52] U.S. Cl. ........................................ 606/57; 606/54; 606/105
[58] Field of Search ............................ 602/20, 21, 22; 606/53–55, 57–59, 105

[56] References Cited

U.S. PATENT DOCUMENTS

| | | | |
|---|---|---|---|
| 4,258,708 | 3/1981 | Gentile | 606/59 X |
| 4,548,199 | 10/1985 | Agee | 606/57 |
| 4,604,997 | 8/1986 | De Bastiani et al. | 606/59 X |
| 4,628,922 | 12/1986 | Dewar | 606/59 X |
| 4,696,293 | 9/1987 | Ciullo | 606/57 |
| 4,730,608 | 3/1988 | Schlein | 606/57 |
| 4,919,119 | 4/1990 | Jonsson et al. | 606/54 |
| 4,922,896 | 5/1996 | Agee et al. | 606/57 X |
| 5,108,394 | 4/1992 | Kurokawa et al. | 606/59 |
| 5,160,335 | 11/1992 | Wagenknecht | 606/59 |
| 5,207,676 | 5/1993 | Canadell et al. | 606/57 X |

FOREIGN PATENT DOCUMENTS

| | | | |
|---|---|---|---|
| 512792 | 11/1992 | European Pat. Off. | 606/54 |
| 2393563 | 2/1979 | France | 606/59 |
| 2674120 | 9/1982 | France | 606/54 |
| 995722 | 12/1983 | U.S.S.R. | 606/55 |
| 9202184 | 2/1992 | WIPO | 606/54 |

*Primary Examiner*—Max Hindenburg
*Assistant Examiner*—Brian E. Hanlon
*Attorney, Agent, or Firm*—McHale & Slavin

[57] ABSTRACT

An external fixation device that allows passive or active flexion/extension range of motion of the proximal interphalangeal joint. The fixation device assures maintenance of congruent proximal interphalangeal joint throughout the flexion/extension arc. The device attaches to orthopedically placed pins in the proximal phalanx and middle phalanx. Components placed between the pins include an adjustable hinge support that is centered over the axis of the joint for articulation of a hinge member. The hinge member allows distraction and/or compression along a longitudinal axis perpendicular to the hinge member. In addition, the device provides for dorsal/volar adjustability by use of alignment pins and an adjustment bolt placed perpendicular to the distraction/compression mechanism. The result is a fully adjustable external fixation device that allows 110 degrees of passive and active motion further allowing for the transient realignment of the subluxed joint providing joint congruency.

10 Claims, 3 Drawing Sheets

ARTICULATING EXTERNAL FIXATION DEVICE

BACKGROUND OF THE INVENTION

1. Field of the Invention

This invention relates to the treatment of proximal interphalangeal joints and, in particular, to a multi-directional external fixation device having an adjustable rotation axis, longitudinal basis, and dorsal attachment mechanism allowing for increased rehabilitation of a joint.

2. Background of the Invention

The treatment of interphalangeal joints can be performed by various methods. The method utilized is usually dependant upon the type of injury as well as surgeon preference. One method of treating the injury is by immobilization wherein a fixation device can be used as a splint. The use of an internal fixation device such as Kirschner wires may be used to restore joint congruity. External fixation devices may be as simple as a stick with tape or as elaborate as an ambulator rotating reduction and fixation splint as described in U.S. Pat. No. 2,391,537 issued to Anderson. U.S. Pat. No. 4,349,017 issued to Sayegh discloses an orthopedic apparatus which involves adjustable assemblies of rods and coupling mechanisms which are attached to different parts of a fractured bone whereby the bone can be manipulated and stabilized into a single configuration.

Articulating external fixation devices permit distant advantages in rehabilitation. The articulation may eliminate the need for postoperative therapy. For instance, the external fixator disclosed in U.S. Pat. No. 4,782,842 issued to Fietti, Jr., discloses a fixation device for the setting of a fractured wrist. The wrist can then be moved through a predetermined path of flexion or extension as a result of the metacarpal being operatively connected to a compound arc gear. Similarly, the use of an external fixation device can be applied to the treatment of interphalangeal joints as disclosed in U.S. Pat. No. 4,608,997 issued to DeBastiani.

What is lacking in the art is an external fixation device that provides a means for centering of the axis fixation device or otherwise adjusting the axis to differences and/or variations between the articulating joints. For this reason the use of prior art devices require exact placement of the external fixation device to assure maintenance of the congruent proximal interphalangeal joint throughout the flexion/extension arc. The placement necessary for the wearer comfort as well as proper rehabilitation. The prior art does not teach a means for dorsal/volar setting location or for longitudinal distraction and compression of the proximal phalanx.

Accordingly, what is needed in the art is an external mini-fixator device that allows for immediate post operative active range of motion which maintains congruent reduction through the flexion/extension arc allowing immediate active and passive motion and further provides for the misalignment of a joint and bi-directional linear, toggle and hinge adjustments. Said device allowing for the exact placement of the external fixation device across the flexion/extension axis to provide wearer comfort as well as proper rehabilitation.

SUMMARY OF THE INVENTION

The instant invention is an external fixation device that allows passive or active flexion/extension range of motion of the proximal interphalangeal joints providing for longitudinal distraction and compression, dorsal and volar relocation, and further provides a dorsal splinting during the acute phase. Once attached, the instant device allows bi-directional, linear, toggle and hinge adjustments. The adjustments allowing the variable treatment modalities for all orthopedic hand surgeons as well as to provide finite tuning for individual accommodation.

The invention comprises a proximal base member that is clamped to at least two spaced apart orthopedic pins attached to the proximal phalanx. Mounted to the base is an adjustable hinge bracket that provides a movable axis for a hinge member. The hinge member is effectively a base for a distraction/compression block that is placed perpendicular to a dorsal/volar relocation block. The dorsal/volar relocation block is attached to the middle phalanx using at least two spaced apart orthopedic pins attached to the middle phalanx.

Installation of the device is performed by placing the a template over the proximal phalanx on the medial side of the proximal phalanx. Two proximal pins are advanced perpendicular to the longitudinal access of the proximal phalanx through both cortices. Once the proximal pins are secured in place, the device is attached to the pins by clamps and preset by aligning an adjustment hinge in the device to the center of the head of the proximal phalanx. Set screws are used on the volar side and with the fixator stabilized, distal pins are then placed through distal pin clamps. Preliminary adjustments are made by aligning the adjustment hinge across the flexion/extension axis followed by adjustment to the longitudinal distraction mechanism and the dorsal volar mechanism. All adjustments are locked by the use of set screws before X-ray and final adjustment.

Accordingly, an objective of the instant invention is to provide an external fixation device which assures maintenance of congruent proximal interphalangeal joints throughout the flexion/extension arc.

Yet another object of the instant invention is to provide a fixation device with an adjustable hinge for exacting placement across the flexion/extension axis even after attachment of proximal axis pins.

Yet still another objective of the instant invention is the provision of a longitudinal distraction and compression adjustment mechanism and a dorsal/volar relocation mechanism.

Still another objective of the instant invention is to provide a means for locking of the hinge member, and/or 110 degree of passive and active motion of the hinge for congruent joint reduction.

Other objects and advantages of this invention will become apparent from the following description taken in conjunction with the accompanying drawings wherein set forth, by way of illustration and example, certain embodiments of this invention. The drawings constitute a part of this specification and include exemplary embodiments of the instant invention and illustrate various objects and features thereof.

DETAILED DESCRIPTION OF THE PREFERRED EMBODIMENT

As required, detailed embodiments of the present invention are disclosed herein, however, it is to be understood that the disclosed embodiments are merely exemplary of the invention which may be embodied in various forms. Therefore, specific functional and structural details disclosed herein are not to be interpreted as limiting, but merely as a basis for the claims and as a representative basis for teaching one skilled in the art to variously employ the present invention in virtually any appropriately detailed structure.

Figure 1:
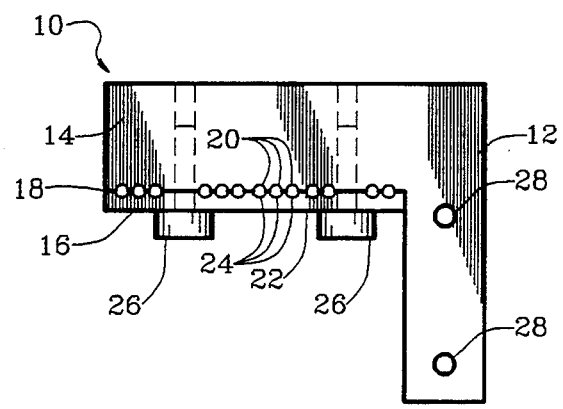
FIG. 1 is a side plan view of the proximal phalanx base mechanism.

Now referring in general to FIGS. 1-5, shown are the individual components that comprise the multi-directional articulating external fixator of the instant invention. Preferred component material is radiolucent aluminum, but it should be noted that any suitable rigid and lightweight material is within the scope of this invention. In particular, FIG. 1 illustrates the proximal base member 10 having an L-shaped bifurcated block 10 defined by a bottom 12 and an elongated stem 14. A first pin clamping surface 16 is disposed along surface 18 of the elongated stem with a plurality of guide ways 20 placed across the surface 18. A separate, opposingly spaced, parallel plate 22 is securably mounted to the elongated stem 14 with a plurality of guide ways 24 corresponding to the stem surface guide ways 20 forming openings, which together with spaced apart mounting bolts 26 having a head formed for wrench or screwdriver actuation, provide a means for clamping at least two spaced orthopedic pins extending perpendicular to the axis of the bone, and attached longitudinally to the proximal phalanx. Mounting holes 28 provide for a hinge bracket securement described hereinafter.

Figure 2:
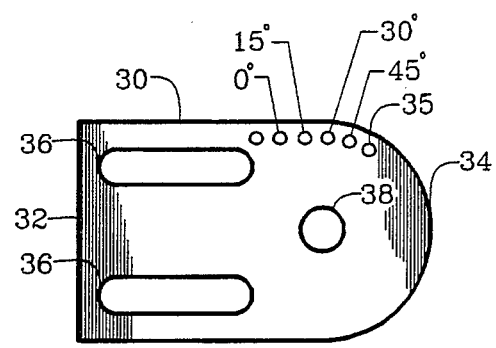
FIG. 2 is a side plan view of the horizontal hinge bracket plate.

FIG. 2 sets forth the hinge bracket 30 used to couple to each side of the proximal base member 10 in conjunction with mounting holes 28. The bracket is formed by two separate and independent plates and 30' having a parallel relation to one another. One plate is set forth for simplicity, the second plate forming a mirror image thereof. Each plate having a mounting end 32 and a hinge end 34. The mounting end 32 having two elongated slots 36 corresponding to the mounting holes 28 of the proximal base member 10 juxtapositioning each plate 30 to the base member 10 on opposite side surfaces thereof by use of an attachment bolt, not shown. An attachment bolt is inserted into slots 36, through mounting holes 28, into the second plate having slots fitted over the protruding bolts with locking nuts, threaded plate, cooperative coupling screw, or the like attachment means. The elongated slots allow for a range of adjustment of the hinge end 34 along a horizontal line and a minute range of vertical adjustment. Hinge end 34 includes a hinge member aperture mounting hole 38 forming an axis of the joint to assure maintenance of the congruent proximal interphalangeal joint throughout the flexion/extension arc. The aperture may be hardened or used for housing a bushing or the like frictionless bearing to provide for effortless articulation of the joint. The flexion/extension axis of the proximal interphalangeal joint lies equidistant from the dorsal distal and palmar articular surface of the primal phalangeal condyle. A plurality of transfixion pin holes 35 are spaced apart along the edge of the bracket allowing control of the flexion/extension range of motion regardless of subsequent joint adjustment.

Figure 3:
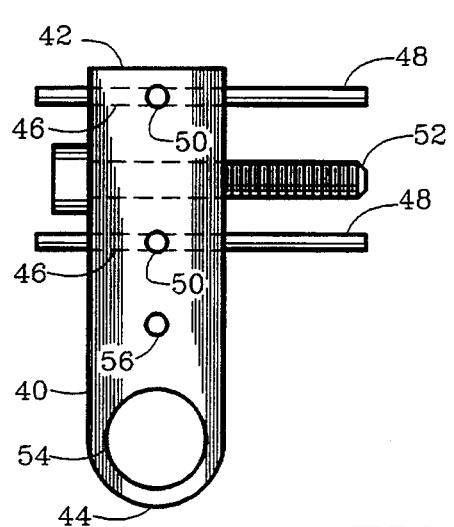
FIG. 3 is a side plan view of the vertical hinge member with alignment pins placed therethrough.

FIG. 3 illustrates the hinge member 40 which is an elongated block defined by a top portion 42 and a bottom portion 44. The top portion 42 includes two apertures 46 disposed therethrough for slidable insertion of alignment pins 48. The alignment pins 48 are made part of the distraction/compression block described hereinafter for the purpose of maintaining the hinge member 40 perpendicular thereto. The alignment pins 48 are secured in position by means of locking screws 50 insertable at a position perpendicular to alignment pin 48 travel. Preferred locking pins are Allen type wrench or screw threaded pins. Similarly, hinge member 40 utilizes a first offset adjustment screw 52 for positioning of the distraction/compression block in relation to the hinge member. Frictionless sleeve bearing 54 provides free articulation of the hinge member 40 in relation to the fixed plates 30. The articulation is set at a predetermined articulation range of 110 degrees to assimilate the human finger movement, the range can be limited by use of a screw 56 that is operatively associated with the plate or the like limiting mannerism. The articulation of the joint motion can be made post application by locking the axis in any position until variable joint motion is desired.

Figure 4:
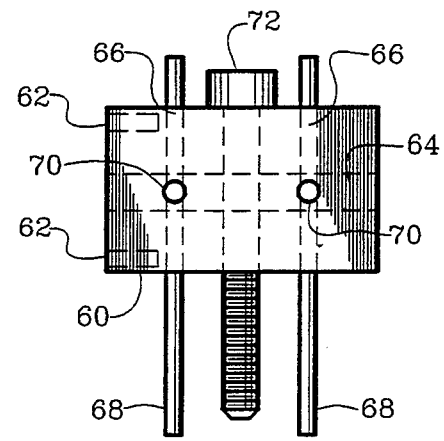
FIG. 4 is a side plan view the distraction/compression mechanism with alignment pins placed therethrough.

FIG. 4 illustrates an adjustment block 60 for distraction and compression of the middle phalanx by use of the hinge member for base support. The distraction/compression block 60 includes the permanent attachment location for alignment pins 48 shown as press fit mounting sockets 62, threaded aperture 64 is operatively associated with the first offset adjustment screw 52. The block includes two apertures 66 disposed therethrough for slidable insertion of alignment pins 68. The alignment pins 68 are made part of the dorsal/volar relocation block described hereinafter. The alignment pins 68 are secured in position by means of locking pins 70 insertable at a position perpendicular to the alignment pin 68 travel. Distraction/compression block 60 utilizes a second offset adjustment screw 72 for positioning of the distraction/compression block in relation to the hinge member.

Figure 5:
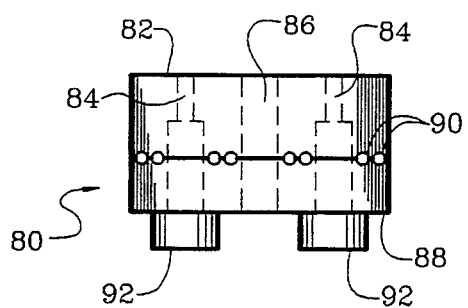
FIG. 5 is a side plan view of the dorsal/volar relocation mechanism for the middle proximal phalanx.

FIG. 5 illustrates the dorsal/volar relocation block 80 having an upper portion 82 including the permanent attachment location for alignment pins 68 shown as the press fit mounting sockets 84. The pins aligning the dorsal/volar relocation block 80 are placed perpendicular to the distraction/compression block 60 using threaded aperture 86 for adjusting a spacial distance therebetween by insertion of second offset adjustment bolt 72 therewith. The relocation block 80 having a lower portion 88 with separate, opposingly spaced, parallel portions forming a mating surface having a plurality of guide ways 90 which, together with spaced apart mounting bolts 92, provide a means for clamping at least two spaced apart orthopedic pins which extend perpendicular to the axis of the bone, and is attached longitudinally to the middle phalanx. The block 80 allows for treatment of dorsal fractures and volar dislocation.

Figure 6:
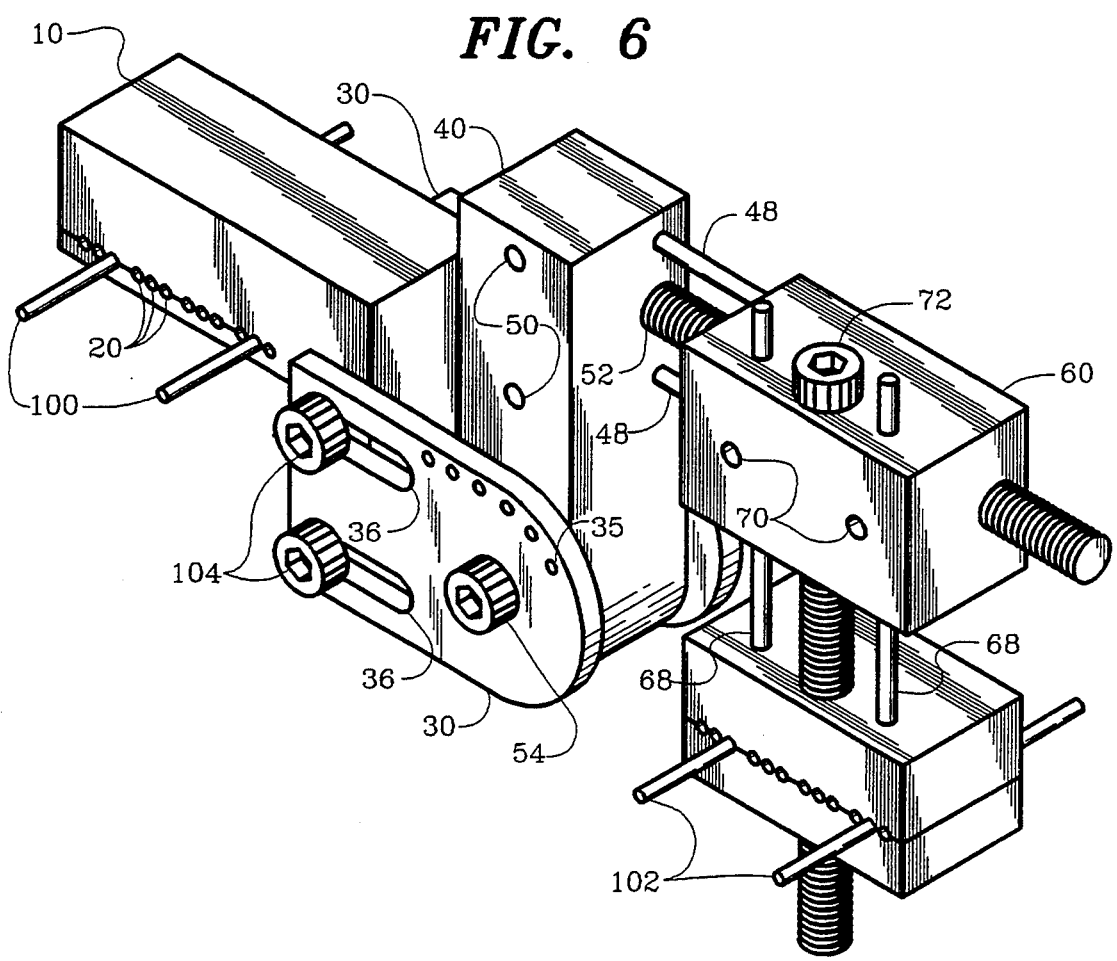
FIG. 6 is a perspective view of the external fixation device of the instant invention with all components coupled.

Now referring to FIG. 6, shown is a perspective view of the instant invention with all components interconnected. The device is dependant upon four cortical pins, two cortical pins 100 for the proximal phalanx and two cortical pins 102 for the middle phalanx. An adjustable template, not shown, is used for placement of the cortical pins. The proximal base member 10 is shown coupled to the proximal cortical pins 100 by guide ways 20 available for pin placement. Pin placement takes into account stability of the base allowing for the spanning of a fracture or size of the individuals phalanx. Hinge bracket 30 is coupled to each side of the proximal base member 10 wherein elongated slots 36 allow for the slidable adjustment of hinge bracket 30 by frictional engagement of attachment bolts 104. The hinge member 40 utilizes a frictionless sleeve bearing, bushing, or the like held in place by mounting bolt 54 to provide free articulation of the hinge member in relation to the fixed plates 30. The transfixion pin holes 35 allow control of the flexion/extension range of motion regardless of subsequent joint adjustment by limiting the rotation to any predetermined position. Each hole 35 allows approximately an additional 15 degree range of motion, complete removal allowing the full 110 degree range of motion. The hinge member 40 slidable along alignment pins 48 using locking screws 50 for pin setting. First offset adjustment screw 52 is used for positioning the distraction/compression block 60 in relation to the hinge member.

The distraction/compression block 60 is slidable along alignment pins 68 using locking screws 70 for alignment pin setting. Second offset adjustment screw 52 is used for positioning the dorsal/volar relocation block 80 in spacial relation to the distraction/compression block 60 injunction with adjustment bolt 72. The dorsal/volar relocation block 80 is shown coupled to the middle cortical pins 102, pin placement takes in account stability of the block allowing for the spanning of a fracture or size of the individuals middle phalanx.

Figure 7:
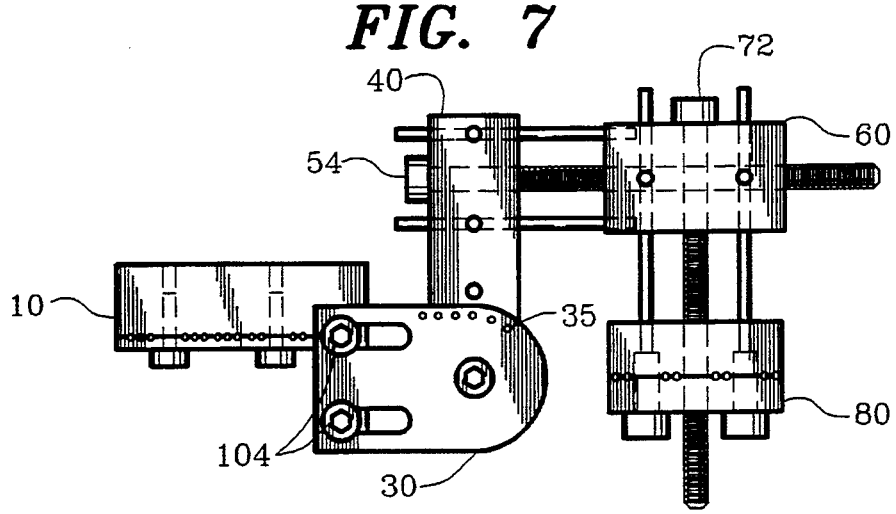
FIG. 7 is a side plan view of the fixation device in the extended mode.
Figure 8:
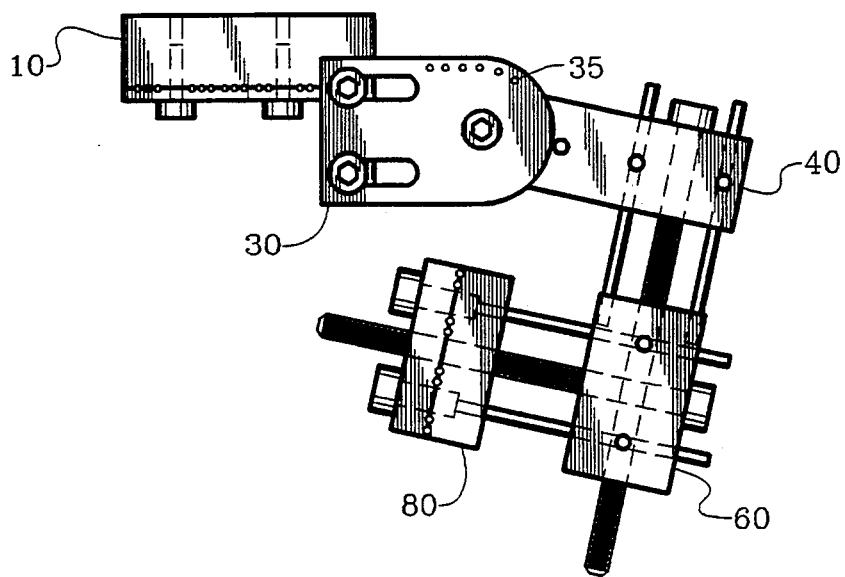
FIG. 8 is a side plan view of the fixation device shown in FIG. 7 articulated to a 110 degree range of motion.
Figure 9:
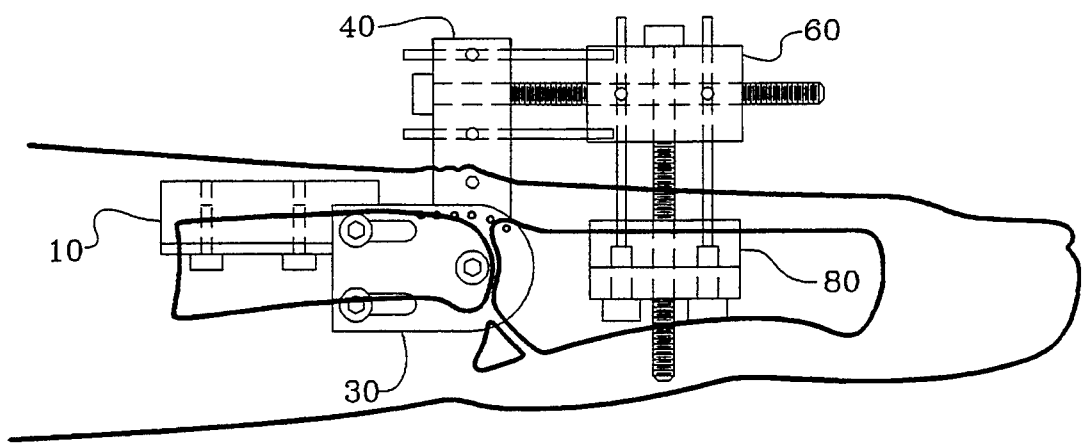
FIG. 9 is a side pictorial view of the fixation device installed upon a finger.

Now referring generally to FIG. 7-9, the instant invention is placed in an extended mode by mounting the proximal base 10 in a parallel relation to the dorsal/volar relocation block 80. FIG. 9 superimposing a finger with the device attached thereto. Attention is directed to the hinge member 40 aperture mounting axis set at the anatomic center of the joint to assure maintenance of the congruent proximal interphalangeal joint throughout the flexion/extension arc. Articulation of the finger causes the dorsal/volar relocation block 80 to rotate about the axis of the hinge member 40. The hinge member 40, previously perpendicular to the proximal base 10 is now shown rotated 110 degrees about the axis. The range predetermined to assimilate the normal range of a human hand. The articulation of the joint motion can be made post application by locking the axis in any position until variable joint motion is desired. Alternatively, one of the transfixion pin holes 35 which are spaced apart every 15 degrees allowing control of the flexion/extension range of motion regardless of subsequent joint adjustment.

Application of the multi-directional fixator is performed once a patient's finger has been anesthetized, prepped and draped, and reduced longitudinally by a surgeon. After reduction, the proximal interphalangeal joint is located and stabilized with a hypodermic needle placed dorsally through the joint. The instant invention is placed on the proximal phalanx on the medial side with a template distal portion placed over the head of the proximal phalanx. Two proximal pins are advanced perpendicular to the longitudinal axis of the proximal phalanx through both cortices. After placement of the proximal pins, the device is applied by aligning the axis of the hinge to the center of the head of the proximal phalanx. The hex screws are then tighten on the volar side. With the device stabilized, the distal pins are placed through the distal pin clamps and the set screws tightened. Adjustment is made to the longitudinal distraction block followed by adjustment to the dorsal/volar block. Once adjusted, all the alignment pins are secured in position by locking of the hex screw. The finger is then available for X-ray of joint alignment for final adjustment if necessary.

It is to be understood that while we have illustrated and described certain forms of our invention, it is not to be limited to the specific forms or arrangement of components herein described and shown. It will be apparent to those skilled in the art that various changes may be made without departing from the scope of the invention and the invention is not to be considered limited to what is shown in the drawings and described in the specification.

What is claimed is:

1. A multi-directional articulating external fixator providing passive or active flexion/extension range of motion for the proximal phalanx and middle phalanx of the human hand, said fixator comprising:

a proximal base member construction from a bifurcated block defined by a top surface, a bottom surface, and two side surfaces, said bifurcated block having a means for clamping at least two spaced apart first orthopedic pins such that said first orthopedic pins are capable of extending perpendicular to the longitudinal axis of a patient's proximal phalanx bone and are capable of being attached longitudinally to the proximal phalanx, said base member having at least two spaced apart coupling holes formed therein;

a hinge bracket defined by two separate and spaced apart plates disposed in parallel relation to one another and juxtapositioned to each side surface of said proximal base member, each said plate having two elongated slots with a mounting bolt being operatively disposed through each elongated slot and into one of said coupling holes for providing slidable movement of said hinge bracket along a plane parallel to the longitudinal axis of the proximal phalanx and providing longitudinal adjustment of a mounting aperture disposed through said hinge bracket;

a first and second offset adjustment screw;

an upright rotatable hinge member operatively associated with said hinge bracket so as to allow an articulation axis of rotation about said mounting aperture, said hinge member having a longitudinal axis and a bore for receiving said first offset adjustment screw through said hinge member;

means for adjustably securing said hinge member in a fixed position;

a rectangular shaped distraction/compression block having a longitudinal axis perpendicular to the longitudinal axis of said hinge member, said distraction/compression block having a threaded aperture for engagement with said first offset adjustment screw thereby providing a means for adjusting spacial distance between said hinge member and said distraction/compression block and providing distraction or compression of the middle phalanx, said block having a bore for receiving said second offset adjustment screw therethrough and a means for aligning said distraction/compression block to said hinge member; and a rectangular shaped dorsal/volar relocation member having a threaded aperture for engagement with said second offset adjustment screw thereby providing a means for adjusting spacial distance between said relocation member and said distraction/compression block and providing vertical displacement of the middle phalanx, said relocation member having a means for being aligned to said distraction/compression block and a means for clamping at least two spaced apart second orthopedic pins such that said second pins are capable of extending perpendicular to the longitudinal axis of the patient's middle phalanx bone and are capable of being attached longitudinally to the middle phalanx.

2. The multi-directional fixation device according to claim 1, wherein each of said means for clamping is further defined as a separate, opposingly spaced, parallel clamping plate securable mounted to one of said base member and said relocation member, with a plurality of guide openings available for clamping at least two orthopedic pins therebetween.

3. The multi-directional fixation device according to claim 2, wherein said elongated slots allow the selective adjustment of said hinge bracket for horizontal and vertical disposition of said hinge member.

4. The multi-directional fixation device according to claim 1 wherein said hinge bracket includes a plurality of transfixion pin holes spaced apart every 15 degrees allowing control of the flexion/extension range of motion regardless of joint adjustment.

5. The multi-directional fixation device according to claim 1, wherein said mounting aperture includes a low friction sleeve bearing providing free rotation of said hinge member.

6. The multi-directional fixation device according to claim 1, wherein each of said means for aligning being at least one alignment pin secured in position by means of a locking element insertable at a position perpendicular to said alignment pin.

7. The multi-directional fixation device according to claim 1 wherein said articulation axis has a predetermined articulation range of 110 degrees.

8. A multi-directional articulating external fixator allowing passive or active flexion/extension range of motion of the proximal interphalangeal joint, said fixator comprising:

a proximal base member defined by an L-shaped bifurcated block having a bottom portion and an elongated stem, a separate, opposingly spaced parallel plate securably mounted to said elongated stem and forming a plurality of first guide openings there between clamping at least two spaced first orthopedic pins which are capable of extending perpendicular to the longitudinal axis of a patient's proximal phalanx bone and are capable of being attached longitudinally to the proximal phalanx, and at least two spaced apart mounting apertures disposed parallel to said first guide openings;

a hinge bracket comprising two separate and independent plates disposed in parallel relation juxtaposed to said proximal base member and having a mounting end and a hinge end, said mounting end having at least two elongated slots corresponding to the mounting apertures of said proximal base member and a means for selectively adjusting said plates thereto, said hinge end having a central aperture disposed therethrough;

a hinge member operatively associated with said hinge bracket and being in the shape of an elongated block having a longitudinal axis, an end surface, a side surface, a top portion and a bottom portion, said top portion including at least two apertures disposed therethrough for slidable insertion of alignment pins and said bottom portion including a sleeve allowing low friction rotation about a horizontal axis;

a distraction/compression block having a longitudinal axis perpendicular to that of said hinge member, the end surface of said hinge member having at least two first alignment pins slidably engagable and operatively associated with said hinge member, said hinge member including a means for locking said first alignment pine in a fixed position, and a means for adjusting a spacial distance between said hinge member and said distraction/compression block; and a dorsal/volar relocation block having an upper surface and a lower surface, said upper surface having at least two second alignment pins slidably engagable and operatively associated with said distraction/compression block, said distraction/compression block including a means for locking said second alignment pins in a fixed position and a means for adjusting a spacial distance between said distraction/compression block and said relocation block, said lower surface having a separate, opposingly spaced parallel plate securably mounted thereto and forming a plurality of second guide openings therebetween clamping at least two spaced second orthopedic pins which are capable of extending perpendicular to the longitudinal axis of the patient's middle phalanx bone and are capable of being attached longitudinally to the middle phalanx.

9. The multi-directional fixation device according to claim 8 wherein said hinge member has articulation of about 110 degrees.

10. The multi-directional fixation device according to claim 9 wherein said hinge member includes a means for stabilizing said middle phalanx in a predetermined position.

* * * * *